United States Patent [19]

Buckman et al.

[11] 4,163,733

[45] Aug. 7, 1979

[54] SYNERGISTIC COMPOSITIONS FOR CORROSION AND SCALE CONTROL

[75] Inventors: John D. Buckman; Gerald D. Mercer; John D. Pera, all of Memphis, Tenn.

[73] Assignee: Buckman Laboratories, Inc., Memphis, Tenn.

[21] Appl. No.: 845,011

[22] Filed: Oct. 25, 1977

[51] Int. Cl.² .............................................. C02B 5/06
[52] U.S. Cl. .................................... 252/180; 252/82; 252/86; 252/181; 252/389 A; 252/396; 210/58; 422/15
[58] Field of Search ........................... 21/2.7 R, 2.7 A; 252/181, 180, 86, 82, 389 A, 396, 105; 210/58

[56] References Cited

U.S. PATENT DOCUMENTS

| | | | |
|---|---|---|---|
| 3,890,228 | 6/1975 | Hwa et al. | 210/58 |
| 3,897,209 | 7/1975 | Harris et al. | 210/58 |
| 3,957,160 | 5/1976 | Ploger et al. | 210/58 |
| 3,963,636 | 6/1976 | Harris et al. | 252/181 |
| 4,029,696 | 6/1977 | Sommer | 210/58 X |

Primary Examiner—Mayer Weinblatt
Attorney, Agent, or Firm—Floyd Trimble

[57] ABSTRACT

Dimethylaminomethylenebis(phosphonic acid) is prepared by reacting dimethylformamide with phosphorous trichloride and treating the reaction mixture with alcohols or glycols and water. The phosphonic acid is combined with water soluble carboxylic acid polymers for use as a corrosion and scale inhibitor in aqueous systems. These compositions may also be combined with phosphorous acid and water soluble zinc salts.

20 Claims, No Drawings

SYNERGISTIC COMPOSITIONS FOR CORROSION AND SCALE CONTROL

This invention relates to compositions, methods of preparing the compositions, and methods of using the compositions for inhibiting the corrosion of metal parts in contact with aqueous systems, for inhibiting the deposition of scale and sludge on the heat transfer surfaces of cooling water systems and boilers, said compositions comprising dimethylaminomethylenebis(phosphonic acid) or water soluble salts thereof, a water soluble polymer having a linear hydrocarbon structure and containing in a side chain carboxylic acid groups or carboxylic acid salt groups with a molecular weight of between 200 and 100,000 with one or more of the following:

A. Water

B. An aqueous solution of phosphorous acid or alkali metal salts thereof

C. An aqueous solution of water soluble zinc salts

It is well known that the operation of commercial and industrial cooling systems is adversely affected by a number of different factors. Of these adverse factors, corrosion of metallic parts coming into contact with the water is probably one of the most serious. If not controlled, corrosion causes the rapid deterioration of the metallic materials of construction used in cooling towers and associated equipment such as pumps, pipelines and valves, causing major losses in overall efficiency of the cooling systems. While control of bleedoff, pH, and other operating variables is helpful in reducing corrosion, chemical treatment of the water is generally the most effective and economical means of minimizing this problem, particularly where conservation of water by means of recycling is necessary or desired.

Cooling water systems are also subject to formation of scale deposits. Scaling can occur when the concentration of a dissolved substance in a cooling water becomes greater than its solubility in the water. It can especially be a problem with a substance that has an inverse solubility curve, that is, a material whose solubility goes down as the temperature goes up. Since water temperatures at or near heat-transfer surfaces are greater than temperatures in the bulk of the system, the solubility of such materials is less in these regions. Consequently, they tend to precipitate and form scales that reduce heat-transfer efficiency.

One principal scale-forming material encountered in cooling water systems is calcium carbonate formed by the decomposition of calcium bicarbonate. This compound not only has an inverse solubility curve, but its solubility is much lower in most typical cooling waters than almost all other potential scale-formers that might be present in these waters. Of course, calcium carbonate is soluble in acidic solutions, and as the pH of a cooling water is lowered, scale generally becomes less of a problem. However, most cooling waters are kept on the alkaline side to reduce corrosion, and thus calcium carbonate scaling remains as a potential problem. Calcium sulfate, calcium phosphate, barium sulfate, and ferric hydroxide can also cause scale. Thus, to be a broadly useful composition, a scale control product must be capable of controlling different scale types.

Waterside problems encountered in boilers and steam systems include the formation of scale and other deposits, corrosion, and foam. Scale and other deposits on heat-transfer surfaces can cause loss in the thermal efficiency of the boiler and can make the temperature of the boiler metal increase. Under scaling conditions, temperatures may go high enough to lead to failure of the metal due to overheating. Corrosion in boilers and steam systems also causes failure of boiler metal and damage to steam and condensate lines.

The principal source of deposits in boilers is dissolved mineral matter in the boiler feedwater. The term "scale" is generally used for deposits that adhere to boiler surfaces exposed to the water, while nonadherent deposits are called "sludge" or "mud." Scale causes more difficulty because the sludge can be purged from the system with the blowdown or can be easily washed out, but scale can normally only be removed by mechanical or chemical cleaning of the boiler.

In natural, untreated water the main sources of scale and sludge are calcium carbonate, calcium sulfate, magnesium hydroxide, and silica. The most common type of scale in boilers is probably calcium carbonate, but the most troublesome is usually calcium sulfate. The latter causes more difficulties because its solubility decreases more rapidly with increasing temperatures than does that of other substances, and the scale it forms is hard, dense, and difficult to remove. On the other hand, calcium carbonate tends to form sludge more than scale, and the calcium carbonate scales that do form are generally softer and easier to remove. Magnesium hydroxide precipitates are not very adherent and tend to form sludges rather than scales.

It is an object of this invention to provide a stable liquid corrosion inhibiting and deposit control product. More specifically, it is an object to prepare a synergistic composition containing a bisphosphonic acid and a polycarboxylic acid which performs for scale control in the threshold range far better than would be expected from the performance of either class of compound alone. It is a further objective of this invention to provide a process for corrosion inhibition and deposit control in cooling water systems.

Further objectives will be evident to those skilled in the art.

All of the compositions of this invention contain dimethylaminomethylenebis(phosphonic acid) or water soluble salts thereof. This compound has the following structure:

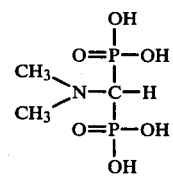

The two phosphonic acid groups on the molecule provide acid hydrogens which can be converted to alkali metal, alkaline earth metal and ammonium salts.

The water soluble polymer also contained in all of the compositions is a linear hydrocarbon structure with side chain carboxylic acid groups and is exemplified by the following structure:

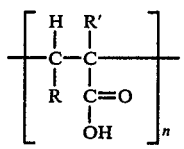

where R is hydrogen or —COOH and R' is hydrogen or methyl. These polymers may be obtained from acrylic acid or methacrylic acid. Polymers of maleic anhydride can be prepared and the anhydride group hydrolyzed with water to provide carboxylic acid groups. Acrylonitrile and acrylamide polymers may also be hydrolyzed with hot alkaline solutions to eliminate ammonia and form carboxylic acid salts. Copolymers of all of the monomers listed may also be prepared and these copolymers may be hydrolyzed to the carboxylic acid groups if the anhydride, amide, or nitrile groups are contained in the copolymer. These polymers may be utilized as the free acid or as water soluble salts such as the alkali metal and alkaline earth metal salts. The polymers used in this invention are commercially available or methods for their preparation are well known in the art.

The phosphorous acid utilized in these compositions may be anhydrous or aqueous solutions containing 50 to 75 percent of the acid.

Water soluble zinc salts which may be utilized include zinc acetate, zinc chloride, zinc nitrate, and zinc sulfate.

The preparation of dimethylaminomethylenebis(phosphonic acid) has been described in U.S. Pat. No. 3,846,420, Nov. 5, 1974. Dimethylformamide was reacted with phosphorous trichloride and then a large excess of water was added. Alternatively, a mixture of phosphorous acid and phosphorous trichloride is reacted with dimethylformamide. In some examples, solvents such as carbon tetrachloride and dioxane are used in the reaction. The yields based on the amount of phosphorous trichloride used vary from 22 to 76 percent. The process described has a number of disadvantages:

1. Even when a solvent is used, the products are pasty or solid and impossible to handle in commercial processes.
2. If a water soluble solvent is used, distillation must be used to isolate the product.
3. Hydrolysis converts every atom of chlorine in the phosphorous trichloride to hydrochloric acid which is so irritating and so toxic that it must also be isolated or neutralized with alkali.
4. The best yield reported is only 76 percent.

In this invention we have reacted dimethylformamide with phosphorous trichloride and about two-thirds the stoichiometric amount of an alcohol or glycol. The reaction was completed utilizing hydrolysis with water. We were surprised that the evolution of hydrogen chloride was greatly reduced and that alcohols and glycols could be converted in high yield to alkyl chlorides and to dichloroalkanes. The yields of dimethylaminomethylenebis(phosphonic acid) based on the weight of phosphorous trichloride used were essentially quantitative in many instances. Although the stoichiometry is not completely understood, the overall reaction may be characterized by the equation

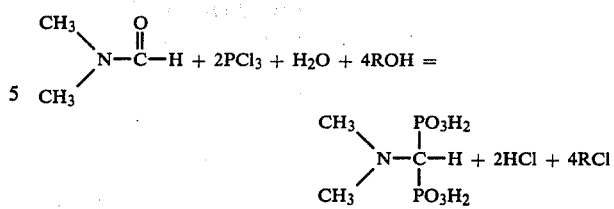

When a solvent is required, the alkyl halide (RCl) or dichloroalkane that is being formed may be added to the mixture when the dimethylformamide and phosphorous trichloride are reacted.

Alcohols and glycols suitable for the preparation of dimethylaminomethylenebis(phosphonic acid) and the corresponding alkyl chlorides and dichloroalkanes include, but are not limited to, methanol, ethanol, 1-propanol, 2-propanol, 1-butanol, isobutanol, sec-butanol, tert-butanol, amyl alcohols, longer chain alcohols with $C_6$ to $C_{18}$ alkyl groups, ethylene glycol, propylene glycol, butylene glycols, diethylene glycol and triethylene glycol.

The advantages of producing dimethylaminomethylenebis(phosphonic acid) by the process of this invention are:

1. Very high yields based on the amount of phosphorous trichloride used are obtained.
2. The toxic and polluting hydrogen chloride is reduced.
3. Valuable chloroalkanes and dichloroalkanes are simultaneously produced with the dimethylaminomethylenebis(phosphonic acid).
4. A wide variety of alcohols and glycols are suitable in the process.
5. Pasty or solid intermediates are eliminated which makes the process useful at commercial scale.

The examples of this invention describe several experiments in which dimethylaminomethylenebis(phosphonic acid) was prepared in good yield using several different glycols and alcohols.

The dimethylaminomethylenebis(phosphonic acid) is usually isolated as an aqueous solution, but it can also be obtained as a crystalline solid. Aqueous solutions of the phosphonic acid or salts of the phosphonic acid can be mixed with solutions of the polymers in water to prepare the composition of this invention. Phosphorous acid, alkali metal phosphites, and water-soluble zinc salts may then be added to the aqueous solutions in varying amounts to prepare the additional compositions described in this invention. When zinc salts are used in the compositions of this invention, it is necessary to decrease the pH of the preparation by addition of the appropriate level of phosphorous acid or another mineral acid to prevent separation of complex zinc salts.

The use of dimethylaminomethylenebis(phosphonic acid) and its alkali metal and ammonium salts for the inhibition of precipitation of insoluble salts from aqueous solutions has been described in U.S. Pat. No. 3,957,160, May 18, 1976. This invention claims that the compound is effective at a molar ratio of $5 \times 10^{-4}$ to $5 \times 10^{-2}$ mols per mol of precipitable salt cation. For dimethylaminomethylenebis(phosphonic acid) these values correspond to ratios of 0.27 to 27 parts of the phosphonic acid per 100 parts of calcium.

Polyacrylic acid, other carboxylic acid polymers and salts of the polymers are also known to be effective in preventing the precipitation of alkaline earth metal salts and iron salts from aqueous solution.

Neither the dimethylaminomethylenebis(phosphonic acid) nor the polymeric carboxylic acids are completely satisfactory as water treatment chemicals. The phosphonic acid is most effective in preventing the precipitation of calcium carbonate, but it is much less effective with regard to precipitation of calcium sulfate, calcium acid phosphate, barium sulfate, and ferric hydroxide. The polymeric carboxylic acids are not effective as corrosion inhibitors and the literature does not have any statements concerning corrosion inhibiting properties of the dimethylaminomethylenebis(phosphonic acid).

We have found that the compositions of this invention can be manufactured efficiently and that these compositions will provide effective corrosion inhibition of metal parts in contact with aqueous systems. Surprisingly, these compositions are more effective in preventing the precipitation of metal salts from aqueous solutions than would be expected from the combinations of the individual products included in the compositions. This synergism is particularly noted when the compositions are used for scale control at threshold treatment levels.

In order to demonstrate the scale inhibiting properties of the compositions of this invention, we have used anti-precipitation tests with super-saturated solutions of calcium carbonate, calcium sulfate, calcium acid phosphate, barium sulfate, and ferric hydroxide. The most convenient test methods are related to the demonstration of a "threshold effect," which is defined as a stabilization of super-saturated solutions of scale forming salts by less than stoichiometric concentrations of the anti-precipitants. The mechanism of this effect currently postulates that the anti-precipitant is adsorbed on the growth site of the scalent crystallite during the process of crystallization. This adsorption alters the growth pattern so that the resultant scalent crystals are formed more slowly and are highly distorted. The retardance of crystal growth rate lowers the amount of solid scalent deposited on surfaces. In addition, the distortion of the crystal structure usually gives the scalent solid a different adherence characteristic and the surfaces then have a decreased amount of scale accumulation.

This invention is further illustrated by the following specific but non-limiting examples.

EXAMPLE 1

A reaction flask was charged with 200 grams of bis(2-chloroethyl) ether and 36.5 grams of dimethylformamide and the mixture was treated with 110 grams of phosphorous trichloride added dropwise at such a rate that the reaction temperature was maintained between 20° and 45° C. After one hour agitation at this temperature, the reaction was treated with 63.6 grams of diethylene glycol which was added at such a rate that the reaction temperature did not exceed 45° C. Agitation was continued for two hours at 30° to 45° C. after the addition was complete. The reaction was warmed slowly to 70° C. and maintained at this temperature for sixteen hours. Twenty grams of water were then added slowly while the temperature was allowed to increase to 95° to 100° C. The mixture was agitated for thirty minutes, after which, an additional charge of 100 grams of water was made. Once again, the reaction was maintained at 95° to 100° C. for thirty minutes before being cooled to 60° C. and separated in a separatory funnel. The lower aqueous layer was steam distilled to remove bis(2-chloroethyl)ether and treated with acetone to precipitate 72.1 grams (76 percent yield) of dimethylaminomethylenebis(phosphonic acid)monohydrate. The bis(2-chloroethyl)ether removed by steam distillation was combined with the organic layer and a total yield of 283.2 grams (97 percent) was obtained.

EXAMPLE 2

A reaction flask was charged with 1200 grams of bis(2-chloroethyl) ether and 220 grams of dimethylformamide and the mixture was treated with 660 grams of phosphorous trichloride added at such a rate that the reaction temperature was maintained between 20° and 45° C. After one hour of agitation at this temperature, the flask was charged with 490 grams of diethylene glycol which was added at such a rate that the temperature did not exceed 45° C. The flask contents were agitated at 20° to 25° C. for sixteen hours and then transferred to a glass-lined, steel autoclave. The autoclave was heated at 155° to 165° C. for twelve hours and a pressure of 50 pounds per square inch was observed. After cooling and venting, the autoclave contents were treated with 180 grams of water and the temperature was allowed to rise to 90° to 95° C. Agitation at this temperature was continued for thirty minutes and then 1500 grams of additional water were added. The reaction mixture was agitated for eight hours and then separated in a separatory funnel. Analysis of the aqueous layer indicated that a yield of 494.6 grams (94.1 percent) of dimethylaminomethylenebis(phosphonic acid) had been obtained. The yield of bis(2-chloroethyl)ether in excess of that added in the beginning of the reaction was 553.6 grams (83.8 percent).

EXAMPLE 3

The procedure of Example 1 was followed except that the dimethylaminomethylenebis(phosphonic acid) in the aqueous solution was determined by titration. A yield of 89.3 percent was obtained. The yield of the bis(2-chloroethyl)ether in excess of that used as solvent was 92.1 percent.

EXAMPLE 4

The procedure of Example 1 was followed except that ethylene dichloride was used in place of bis(2-chloroethyl)ether and ethylene glycol (37.2 grams) was used in place of diethylene glycol. The yield of ethylene dichloride in excess of that used as solvent was 50.8 percent and the yield of dimethylaminomethylenebis(phosphonic acid) was 87.7 percent.

EXAMPLE 5

The procedure of Example 1 was followed except that ethylene dichloride was used in place of bis(2-chloroethyl ether and n-butyl alcohol (88.8 grams) was used in place of diethylene glycol. The yield of n-butyl chloride was 39.2 percent and the yield of dimethylaminomethylenebis(phosphonic acid) was 75.5 percent.

EXAMPLE 6

The procedure of Example 1 was followed except that n-dodecyl chloride was used in place of bis(2-chloroethyl)ether and n-dodecyl alcohol (224 grams) was used in place of diethylene glycol. The yield of dodecyl chloride in excess of that used as solvent was 82 percent and the yield of dimethylaminomethylenebis(phosphonic acid) was 56.9 percent.

EXAMPLE 7

A composition containing 15 percent of dimethylaminomethylenebis(phosphonic acid) and 15 percent of poly(acrylic acid) in water was prepared by mixing 47.5 grams of an aqueous solution containing 31.6 percent of the trisodium salt of dimethylaminomethylenebis(phosphonic acid), 35.2 grams of an aqueous solution containing 42.6 percent of poly(acrylic acid)-(molecular weight—3000), and 17.3 grams of water.

EXAMPLE 8

The solutions of dimethylaminomethylenebis(phosphonic acid) and poly(acrylic acid) referred to in Example 7 were used to prepare two formulations. The first contained 17.0 percent each of the phosphonate and polymer and the second solution contained 20.0 percent of the phosphonate and 13.0 percent of the polymer. Each of these solutions was then mixed with an aqueous solution containing 70 percent of phosphorous acid to prepare the following compositions:

| Number | Phosphonate Percent | Polymer Percent | Phosphorous acid Percent |
|---|---|---|---|
| 8A | 16.2 | 16.2 | 3.5 |
| 8B | 15.3 | 15.3 | 7.0 |
| 8C | 14.4 | 14.4 | 10.5 |
| 8D | 19.0 | 12.4 | 3.5 |
| 8E | 18.0 | 11.7 | 7.0 |
| 8F | 17.0 | 11.0 | 10.5 |

EXAMPLE 9

A composition was prepared using a 31.0 percent solution of the trisodium salt of dimethylaminomethylenebis(phosphonic acid), a 45.6 percent solution of poly(acrylic acid) with a molecular weight of 3300–3500, 70 percent phosphorous acid, 50 percent sodium hydroxide and water to provide the following concentrations:

| | |
|---|---|
| Phosphonate | 16.5 percent |
| Poly(acrylic acid) | 11.0 percent |
| Phosphorous acid | 6.0 percent |
| Sodium hydroxide | 5.5 percent |

The corrosion inhibiting properties of solutions of this composition with zinc chloride were determined in Example 11.

EXAMPLE 10

One hundred grams of a solution containing 20 percent of the trisodium salt of dimethylaminomethylenebis(phosphonic acid) and 13 percent of 3300–3500 molecular weight poly(acrylic acid) were mixed with 15 grams of 37 percent hydrochloric acid and 40 grams of a 50 percent solution of zinc chloride. The corrosion inhibiting results using this composition are included in Example 11.

EXAMPLE 11

This example illustrates the corrosion-inhibiting properties of the compositions. The test apparatus included a sump, a flow circuit, a circulating pump, and a heater. A test fluid was prepared to approximate a moderately hard well water concentrated 4 times which did not come in contact with any metal except for test coupons placed within the circuit in a manner simulating flow, impingement, and sump conditions. The test coupons were 1010 mild steel, and the circulating solution had a calcium hardness as $CaCO_3$ of 270 parts per million, a magnesium hardness as $CaCO_3$ of 170 parts per million, chlorie as NaCl of 500 parts per million, and sulfate as $Na_2SO_4$ of 624 parts per million.

The temperature during the test was maintained at about 55° C., and the pH varied from 7 to 9. The test fluid was circulated continuously through the system containing the coupons for a period of seven days. The steel coupons were removed and examined for scale. No significant amount of scale was observed on any of the coupons protected by the compositions of this invention. The coupons were then cleaned and weighed and the corrosion rates calculated as mils per year. One mil per year loss is equal to a volume decrease of 0.001 inch per year or 0.0254 millimeter per year. The corrosion rates are included in Table 1.

Table 1

Corrosiion test results using the compositions of Examples 7, 8, 9, and 10

| Corrosion inhibiting composition Example No | active ingredient | Zinc* added | Corrosion rate in mils per year | | |
|---|---|---|---|---|---|
| | Parts per million | | Current | Impingement | Sump |
| 7 | 30 | — | 48 | 99 | 32 |
| 7 | 45 | — | 44 | 73 | 38 |
| 7 | 60 | — | 27 | 55 | 25 |
| 7 | 60 | 2 | 15 | 20 | 16 |
| 7 | 60 | 4 | 10 | 18 | 9 |
| 7 | 60 | 6 | 12 | 15 | 19 |
| 8A | 36 | — | 18 | 26 | 20 |
| 8B | 38 | — | 15 | 18 | 14 |
| 8C | 40 | — | 29 | 38 | 29 |
| 8D | 35 | — | 20 | 33 | 31 |
| 8E | 37 | — | 10 | 15 | 15 |
| 8F | 38 | — | 11 | 17 | 11 |
| 9 | 33.5 | 3.4 | 11 | 23 | 9 |
| 9 | 33.5 | 6.7 | 4 | 3 | 4 |
| 9 | 33.5 | 10.1 | 3 | 3 | 3 |
| 9 | 33.5 | 13.4 | 2 | 3 | 2 |
| 10 | 5.4 | 1.5 | 27 | 112 | 41 |
| 10 | 10.7 | 3.1 | 10 | 6 | 8 |
| 10 | 16.0 | 4.6 | 9 | 24 | 14 |
| 10 | 21.3 | 6.2 | 2 | 2 | 1 |
| 10 | 31.9 | 9.3 | 2 | 2 | 2 |
| Control | — | — | 56 | 186 | 44 |

*The composition of Example 10 contained zinc in the concentrated formulations.

The results of these tests clearly demonstrate that compositions of this invention have excellent corrosion inhibiting properties when tested against steel coupons in a very aggressive aqueous system.

EXAMPLE 12

The compositions of this example were tested as scale inhibiting preparations in Examples 13–17.

Table 2

| | Trisodium salt of dimethylamino-methylenebis(phosphonic acid) Percent | Poly(acrylic acid) Mol Wt = 3000–5000 Percent | Phosphoric acid Percent | Phosphorous acid Percent |
|---|---|---|---|---|
| | (Based on total of active materials) | | | |
| A | 100 | — | — | — |
| B | — | 100 | — | — |
| C | 75 | 25 | — | — |
| D | 50 | 50 | — | — |
| E | 25 | 75 | — | — |
| F | 61 | 39 | — | — |
| G | 48 | 32 | 20 | — |
| H | 43 | 28 | 29 | — |
| I | 54 | 36 | — | 10 |
| J | 49 | 32 | — | 19 |
| K | 72 | 28 | — | — |
| L | 81 | 19 | — | — |
| M | 50 | 32 | — | 18 |

EXAMPLE 13

Compositions of this invention included in Table 2 were compared for inhibition of calcium carbonate with the trisodium salt of dimethylaminomethylenebis(phosphonic acid) and poly(acrylic acid). The test was conducted by adding to a bottle 100 milliliters of 0.04 percent solution of calcium hydroxide freshly prepared from recently boiled demineralized water. The compositions being tested were added to provide the calculated concentration desired. Then, 100 milliliters of a 0.05 percent solution of sodium bicarbonate prepared from recently boiled demineralized water was added to the bottle. The final volume was adjusted to 220 milliliters and the solutions were allowed to stand for 18 hours at room temperature. The contents of the bottles were filtered through Whatman No. 4 filter paper, and the filtered solutions were analyzed for calcium content using an atomic absorption instrument or an EDTA titration procedure. The concentration was 98 parts per million calcium which is equivalent to 245 parts per million of calcium carbonate. The percentage inhibition of precipitation was calculated by dividing the calcium content of the filtrate by 98 and multiplying by 100. The results obtained are included in Table 3.

The results of these tests show that dimethylaminomethylenebis(phosphonic acid)(A) and poly(acrylic acid)(B) will inhibit the precipitation of calcium carbonate. When the two are combined in various proportions (C, D, E, F), the antiprecipitant properties are maintained and the results with F actually indicate that the overall effectiveness is better than that expected from the combination (synergism). When the phosphonate and poly(acrylic acid) are combined with phosphoric acid (G and H), the antiprecipitant property is greatly decreased. However, combinations with phosphorous acid (I and J) maintain the high level of antiprecipitant effect and the corrosion inhibiting property of the composition containing phosphorous acid was demonstrated in Example 11. The startling difference observed with compositions containing phosphoric and phosphorous acids is completely unexpected because of the similarity of the two acids and the relative lack of information in the literature concerning the use of phosphorous acid in water treatment chemical compositions.

Table 3

Results of antiprecipitation tests with calcium carbonate

| Concentration Parts per million | A | B | C | D | E | F | G | H | I | J |
|---|---|---|---|---|---|---|---|---|---|---|
| | | | | Percent inhibition | | | | | | |
| 1 | 16 | 7 | 10 | 16 | 16 | 18 | — | — | 14 | 13 |
| 2 | 31 | 25 | 28 | 39 | 36 | 35 | 33 | 27 | 27 | 30 |
| 3 | 43 | 19 | 48 | 73 | 61 | 55 | — | — | 43 | 45 |
| 4 | 67 | 99 | 80 | 84 | 74 | 78 | 47 | 35 | 55 | 61 |
| 5 | 83 | 100 | 88 | 89 | 82 | 95 | — | — | 70 | 79 |
| 6 | 98 | 97 | 85 | 85 | 82 | 98 | 53 | 40 | 90 | 92 |
| 7 | 94 | 95 | 85 | 85 | 85 | 99 | — | — | 92 | 97 |
| 8 | 99 | 97 | 85 | 83 | 88 | 96 | 54 | 42 | 92 | 97 |

EXAMPLE 14

The compositions included in Table 2 were tested for inhibition of calcium sulfate scale. This test was conducted by mixing in a bottle 10 milliliters of a solution containing 162.9 grams of calcium chloride per liter of solution (prepared with deionized water) and the desired volume of inhibitor stock solution to provide the desired concentration in a final total volume of 175 milliliters. The pH was then adjusted with dilute HCl or dilute NaOH solutions to 7.0. Twenty-five milliliters of $Na_2SO_4$ solution containing 83.45 grams of $Na_2SO_4$ per liter of solution was added to the bottle. The final volume was adjusted to 175 milliliters if necessary and the bottle was shaken on a gyratory shaker table at room temperature for 18 hours. Each bottle contained 10,000 parts per million of calcium sulfate.

After shaking, the contents of the bottles were filtered through Whatman No. 4 filter paper and the filtrates were analyzed for calcium content using an atomic absorption spectrophotometer or an EDTA titration procedure. It was necessary to dilute the filtrate before analysis if the calcium content was high. The percentage inhibition of precipitation was calculated by dividing the calcium content of the filtrate by 2940 and multiplying by 100. The results are included in Table 4.

The results included in Table 4 show that the trisodium salt of dimethylaminomethylenebis(phosphonic acid)(A) is not an effective control agent for calcium sulfate. Although poly(acrylic acid) was consistent, it did not inhibit precipitation of calcium sulfate by as much as 70 percent as 10 parts per million. When various combinations of the phosphonic acid and polymer were used (C, D, E, F, K, L), excellent inhibition was obtained in every case. For example, composition D gave 97 percent inhibition of the calcium sulfate at one part per million. All of the combinations were much more effective than would have been expected from the test results with either component, and there is no doubt that synergism was demonstrated in these tests.

Table 4

Results of antiprecipitation tests with calcium sulfate

| Concentration Parts per million | Composition | | | | | | |
|---|---|---|---|---|---|---|---|
| | A | B | C | D | E | F | K | L |
| | Percent inhibition | | | | | | |
| 1 | — | 62 | — | 97 | — | — | — | — |
| 2 | — | 59 | — | 97 | — | — | — | — |
| 3 | — | 59 | 97 | 86 | 62 | 93 | 79 | 72 |
| 4 | — | 69 | 97 | 90 | 55 | 90 | 86 | 72 |
| 5 | 7 | 69 | 86 | 97 | 62 | 90 | 97 | 83 |
| 6 | 10 | 66 | 86 | 90 | 79 | 100 | 100 | 100 |
| 7 | 7 | 55 | 90 | 97 | 76 | 100 | 100 | 100 |
| 8 | 0 | 66 | 83 | 94 | 90 | 100 | 100 | 100 |
| 9 | 14 | 66 | 93 | 94 | 89 | 100 | 100 | 100 |
| 10 | 3 | 62 | 79 | 97 | 90 | 100 | 100 | 100 |

EXAMPLE 15

The compositions included in Table 2 were tested for inhibition of barium sulfate scale. The same procedure as that described in Example 13 was used except that the concentration of barium sulfate present was 255 parts per million. The barium solution used contained 5.35 grams of $BaCl_2 \cdot 2H_2O$ per liter of solution and the sulfate solution contained 1.24 grams of $Na_2SO_4$ per liter of solution. After filtration, the solutions were analyzed for barium using atomic absorption spectrophotometry. The results of the tests are included in Table 5.

The results from the table show that the trisodium salt of dimethylaminomethylenebis(phosphonic acid)(A) is not a good inhibitor for barium sulfate precipitation but that poly(acrylic acid) is a good inhibitor. Combinations of the two materials (C, D, E, F) show intermediate effectiveness. However, the outstanding feature of Table 5 is related to the excellent and unexpected results obtained when phosphorous acid is added to the combination of the phosphonic acid and poly(acrylic acid)(M). Composition M gave 75 percent inhibition at a concentration as low as 3 parts per million and 100 percent at 6 parts per million.

Table 5

Results of antiprecipitation tests with barium sulfate

| Concentration Parts per million | Composition | | | | | | |
|---|---|---|---|---|---|---|---|
| | A | B | C | D | E | F | M |
| | Percent inhibition | | | | | | |
| 3 | 7 | 17 | 7 | 0 | 7 | 7 | 75 |
| 6 | 7 | 37 | 12 | 33 | 27 | 25 | 100 |
| 9 | 7 | 43 | 23 | 30 | 47 | 52 | 100 |
| 12 | 7 | 70 | 23 | 33 | 57 | 71 | 100 |
| 15 | 7 | 94 | 77 | 67 | 87 | 80 | 100 |
| 18 | 3 | 96 | 37 | 33 | 83 | 91 | 100 |
| 21 | 3 | 100 | 40 | 50 | 77 | 91 | 100 |
| 24 | 3 | 90 | 57 | 63 | 67 | 88 | 100 |
| 27 | 0 | 96 | 57 | 67 | 90 | 87 | 100 |
| 30 | 3 | 96 | 63 | 73 | 87 | 100 | 100 |

Solution M contained 50 percent of trisodium dimethylaminomethylenebisphosphonate, 32 percent of poly(acrylic acid) and 18 percent of phosphorous acid on a 100 percent active basis as described in Table 2.

EXAMPLE 16

The compositions included in Table 2 were tested for inhibition of calcium acid phosphate precipitation. The same procedure as that described in Example 13 was used except that the concentration of calcium acid phosphate ($CaHPO_4$) present was 300 parts per million. The calcium solution contained 4.89 grams of $CaCl_2$ per liter of solution and the phosphate solution contained 4.70 grams of $Na_2HPO_4 \cdot 7H_2O$ per liter of solution. The filtered solutions were analyzed by an EDTA titration procedure. The results of these tests are included in Table 6.

Poly(acrylic acid)(B) is a good inhibitor of $CaHPO_4$ but the trisodium salt of dimethylaminomethylenebis(phosphonic acid) is only fair in effectiveness. Combinations of the two materials (C, D, E) provided good inhibition of $CaHPO_4$ at intermediate concentrations and Composition E was even more effective than would be expected from combination of the two materials.

Table 6

Results of antiprecipitation tests with calcium acid phosphate

| Concentration Parts per million | Composition | | | | |
|---|---|---|---|---|---|
| | A | B | C | D | E |
| | Percent inhibition | | | | |
| 3 | 0 | 17 | 0 | 0 | 0 |
| 6 | 0 | 13 | 0 | 0 | 0 |
| 9 | 73 | 37 | 57 | 17 | 30 |
| 12 | 73 | 100 | 60 | 80 | 100 |
| 15 | 63 | 100 | 100 | 77 | 100 |
| 18 | 67 | 100 | 87 | 77 | 100 |
| 21 | 63 | 100 | 87 | 83 | 100 |
| 24 | 70 | 100 | 90 | 100 | 100 |
| 27 | 60 | 100 | 83 | 100 | 100 |
| 30 | 70 | 100 | 87 | 100 | 100 |

EXAMPLE 17

Inhibition of ferric hydroxide precipitation by compositions included in Table 2 was evaluated. A solution containing 14.5 grams of ferric chloride ($FeCl_3$) per liter of solution was diluted 1 to 50 with deionized water. One hundred milliliters of the dilute solution were mixed with stock solutions of compositions A, B, and D. The volume was made to 200 milliliters, and the pH was adjusted to 9.0 with sodium hydroxide solution. The bottles were allowed to stand for 24 hours and were observed for presence of a brown-orange precipitate of ferric hydroxide. Concentrations of 20 parts per million of A and B were required to inhibit precipitation but only 15 parts per million of composition D were required to inhibit precipitation of the ferric hydroxide.

EXAMPLE 18

A composition similar to Composition D in Table 2 was prepared by mixing a solution of dimethylaminomethylenebis(phosphonic acid) and a solution of a polymer prepared by polymerizing acrylonitrile and hydrolyzing the polymer with sodium hydroxide to a mixture of sodium polyacrylate and polyacrylamide. The solution was formulated so that approximately equal amounts of the phosphonic acid and polymer were present. This composition was effective as an antiprecipitant and as a corrosion inhibitor.

EXAMPLE 19

A composition similar to Composition D in Table 2 was prepared by mixing a solution of dimethylaminomethylenebis(phosphonic acid) and a solution of a polymer prepared by polymerizing maleic anhydride and subsequently hydrolyzing the anhydride group to carboxylic acid groups with sodium hydroxide. The molecular weight of the polymer was in the range of 800 to 2000. The solution was formulated so that approximately equal amounts of the phosphonic acid and polymer were present. This composition was effective as an antiprecipitant and as a corrosion inhibitor.

EXAMPLE 20

A composition was prepared from an aqueous solution of the trisodium salt of dimethylaminomethylenebis(phosphonic acid), an aqueous solution of poly(acrylic acid) having a molecular weight of 4000, an aqueous solution containing 70 percent phosphorous acid, an aqueous solution containing 50 percent sodium hydroxide, and water. The concentration present was 17 percent of the trisodium salt of dimethylaminomethylenebis(phosphonic acid), 11 percent of poly(acrylic acid), 6 percent of phosphorous acid, and 5.5 percent of sodium hydroxide. This composition was effective as an antiprecipitant and as a corrosion inhibitor.

EXAMPLE 21

A corrosion and scale inhibiting composition was prepared by mixing 100 grams of an aqueous solution containing 20 percent of the trisodium salt of dimethylaminomethylenebis(phosphonic acid) and 13 percent of poly(acrylic acid) having a molecular weight of 3200, 15 grams of 35 percent hydrochloric acid, and 50 grams of an aqueous solution containing 50 percent of zinc chloride.

EXAMPLE 22

A corrosion and scale inhibiting composition was prepared by mixing 100 grams of an aqueous solution containing 18 percent of the trisodium salt of dimethylaminomethylenebis(phosphonic acid), 11.7 percent of poly(acrylic acid) having a molecular weight of 3200, and 7 percent of phosphorous acid, 25 grams of 37 percent hydrochloric acid solution, and 50 grams of an aqueous solution containing 50 percent of zinc chloride.

While particular embodiments of the invention have been described, it will be understood, of course, that the invention is not limited thereto since many modifications may be made; and it is, therefore, contemplated to cover by the appended claims any such modifications as fall within the spirit and scope of the invention.

The invention having thus been described, what is claimed and desired to be secured by Letters Patent is:

1. A corrosion and scale inhibiting composition consisting essentially of on a weight basis: about 10 to about 90% dimethylaminoethylenebis-(phosphonic acid) or a water-soluble salt thereof, a water-soluble polymer having a linear hydrocarbon structure with side chain carboxylic groups exemplified by the structure:

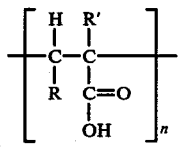

wherein R is hydrogen or —COOH and R' is hydrogen or methyl in an amount varying from about 10 to about 90% and one or more of the following:
A. Water
B. about 0 to 25% of an aqueous solution of phosphorous acid or an alkali metal salt thereof, or
C. about 1.5 to about 13.5% of an aqueous solution of a water soluble zinc salt.

2. The composition of claim 1 wherein the water soluble polymer is poly(acrylic acid).

3. The composition of claim 1 wherein the water soluble polymer is poly(methacrylic acid).

4. The composition of claim 1 wherein the water soluble polymer is hydrolyzed poly(maleic anhydride).

5. The composition of claim 1 wherein the water soluble polymer is hydrolyzed polyacrylonitrile.

6. The composition of claim 1 wherein the water soluble polymer is hydrolyzed polyacrylamide.

7. The composition of claim 1 wherein the dimethylaminomethylenebis (phosphonic acid) and water soluble polymer are dissolved in water.

8. The composition of claim 1 wherein the dimethylaminomethylenebis (phosphonic acid) and water soluble polymer are combined with aqueous phosphorous acid.

9. The composition of claim 1 wherein the dimethylaminomethylenebis (phosphonic acid) and water soluble polymer are combined with aqueous zinc chloride and hydrochloric acid.

10. The composition of claim 1 wherein the dimethylaminomethylenebis (phosphonic acid) and water soluble polymer are combined with phosphorous acid, zinc chloride, hydrochloric acid, and water.

11. A process for inhibiting corrosion and scaling of metal surfaces in water systems consisting essentially in adding to water in said systems an effective amount of a composition consisting essentially of on a weight basis: about 10 to about 90% dimethylaminomethylenebis (phosphonic acid) or a water-soluble salt thereof, a water-soluble polymer having a linear hydrocarbon structure with side chain carboxylic acid groups exemplified by the structure:

$$\left[\begin{array}{cc} H & R' \\ | & | \\ -C-C- \\ | & | \\ R & C=O \\ & | \\ & OH \end{array}\right]_n$$

wherein R is hydrogen or —COOH and R' is hydrogen or methyl in an amount varying from about 10 to about 90% and one or more of the following:
A. Water
B. about 0 to 25% of an aqueous solution of phosphorous acid or an alkali metal salt thereof, or
C. about 1.5 to about 13.5% of an aqueous solution of a water-soluble zinc salt.

12. A process for inhibiting corrosion and scaling of metal surfaces in water systems according to claim 11 consisting essentially in adding to water in said systems from 0.5 to 1000 parts per million parts of water of the composition as defined in claim 11.

13. A process for inhibiting corrosion and scaling of metal surfaces in water systems according to claim 11 consisting essentially in adding to water in said systems an effective amount of the composition as defined in claim 11 wherein the water soluble polymer is poly(acrylic acid).

14. A process for inhibiting corrosion and scaling of metal surfaces in water systems according to claim 11 consisting essentially in adding to water in said systems an effective amount of the composition as defined in claim 11 wherein the water soluble polymer is poly(acrylic acid) and the composition phosphorous acid.

15. A process for inhibiting corrosion and scaling of metal surfaces in water systems according to claim 11 consisting essentially in adding to water in said systems an effective amount of the composition as defined in claim 11 wherein the water soluble polymer is poly(acrylic acid) and the composition contains zinc chloride.

16. A process for inhibiting corrosion and scaling of metal surfaces in water systems according to claim 11 consisting essentially in adding to water in said systems an effective amount of the composition as defined in claim 11 wherein the water soluble polymer is poly(acrylic acid) and the composition contains phosphorous acid, zinc chloride, and hydrochloric acid.

17. A process for inhibiting corrosion and scaling of metal surfaces in water systems according to claim 11 consisting essentially in adding to water in said systems from 0.5 to 1000 parts per million of the composition as defined in claim 11 comprising dimethylaminomethylenebis(phosphonic acid), poly(acrylic acid), and water.

18. A process for inhibiting corrosion and scaling of metal surfaces in water systems according to claim 11 consisting essentially in adding to water in said systems from 0.5 to 1000 parts per million of the composition as defined in claim 11 comprising dimethylaminomethylenebis(phosphonic acid), poly(acrylic acid), phosphorous acid, and water.

19. A process for inhibiting corrosion and scaling of metal surfaces in water systems according to claim 11 consisting essentially in adding to water in said systems from 0.5 to 1000 parts per million of the composition as defined in claim 11 comprising dimethylaminomethylenebis(phosphonic acid), poly(acrylic acid), zinc chloride, hydrochloric acid, and water.

20. A process for inhibiting corrosion and scaling of metal surfaces in water systems according to claim 11 consisting essentially in adding to water in said systems from 0.5 to 1000 parts per million of the composition as defined in claim 11 comprising dimethylaminomethylenebis(phosphonic acid), poly(acrylic acid), phosphorous acid, zinc chloride, hydrochloric acid, and water.

* * * * *